United States Patent [19]

Goulait et al.

[11] Patent Number: 5,380,313

[45] Date of Patent: Jan. 10, 1995

[54] LOOP FASTENING MATERIAL FOR FASTENING DEVICE AND METHOD OF MAKING SAME

[75] Inventors: David J. K. Goulait, Cincinnati, Ohio; Jerry E. Carstens, Germantown, Tenn.

[73] Assignee: The Proctor & Gamble Company, Cincinnati, Ohio

[21] Appl. No.: 821,665

[22] Filed: Jan. 16, 1992

Related U.S. Application Data

[63] Continuation-in-part of Ser. No. 382,516, Jul. 19, 1989, abandoned, which is a continuation-in-part of Ser. No. 64,896, Jun. 19, 1987, Pat. No. 4,854,984.

[51] Int. Cl.⁶ .................. A61F 13/15; A61F 13/20
[52] U.S. Cl. ..................... 604/391; 604/358; 604/384; 604/385.1; 604/386; 604/389; 604/390; 24/448; 428/101; 428/163; 428/286
[58] Field of Search ............. 604/386, 389, 390, 391, 604/385.1, 385.2, 384, 379, 380, 383, 358; 2/DIG. 6; 428/100, 101, 163, 286; 24/444, 447, 448, 450

[56] References Cited

U.S. PATENT DOCUMENTS

| | | |
|---|---|---|
| 1,917,456 | 7/1933 | Mickelson . |
| 2,021,352 | 11/1935 | Eustis . |
| 2,193,052 | 3/1940 | Atwater . |
| 2,434,111 | 1/1948 | Hawley, Jr. et al. . |
| 2,547,880 | 4/1951 | Meyer et al. . |
| 2,978,006 | 4/1961 | Clemens . |
| 3,245,407 | 4/1966 | Mason . |
| 3,425,888 | 2/1969 | Kellicutt . |
| 3,530,023 | 9/1970 | Schutte et al. . |
| 3,577,607 | 5/1971 | Ikoma . |
| 3,639,917 | 8/1972 | Althouse . |
| 3,715,415 | 2/1973 | Erb . |
| 3,800,796 | 4/1974 | Jacob ............................ 604/390 |
| 3,860,003 | 4/1989 | Buell . |
| 3,913,183 | 10/1975 | Brumlik . |
| 3,943,981 | 3/1976 | De Brabander . |
| 3,955,575 | 5/1976 | Okuda . |
| 3,959,051 | 5/1976 | Schirmer . |
| 4,116,892 | 9/1978 | Schwarz . |
| 4,223,059 | 9/1980 | Schwarz . |
| 4,303,571 | 12/1981 | Jansen et al. . |
| 4,377,431 | 3/1983 | Chodosh . |
| 4,429,002 | 1/1984 | Fukada et al. . |

(List continued on next page.)

FOREIGN PATENT DOCUMENTS

| | | |
|---|---|---|
| 0233364A2 | 8/1987 | European Pat. Off. . |
| 0258015 | 3/1988 | European Pat. Off. . |
| 0295957 | 12/1988 | European Pat. Off. . |
| 0341993A1 | 11/1989 | European Pat. Off. . |
| 2088069 | 1/1972 | France . |
| 59-88903 | 5/1984 | Japan . |

*Primary Examiner*—Randall L. Green
*Assistant Examiner*—P. Zuttarelli
*Attorney, Agent, or Firm*—Stephen P. Kearney; Steven W. Miller; E. Kelly Linman

[57] ABSTRACT

A laminated loop fastening material for a refastenable mechanical fastening system, the loop fastening material being capable of engaging a complementary hook fastening material. The loop fastening material is formed by a method comprising the steps of: providing a first lamina and a second lamina, the first lamina having pleats and being fibrous; providing a first roll and a second roll having mutually parallel axes and defining a nip therebetween, the first roll having a plurality of circumferential grooves and lands intermediate the grooves; passing the first lamina and the second lamina through the nip in face to face relation, whereby said first lamina faces the first roll; transversely registering the pleats of the first lamina with the grooves of the first roll; pressing the first roll and the second roll together about the plane generally perpendicular to and connecting the axes of the first roll and the second roll so that the first lamina and the second lamina contact each other at a position corresponding to the lands; and bonding the laminae together at the positions of contact.

3 Claims, 6 Drawing Sheets

U.S. PATENT DOCUMENTS

| | | |
|---|---|---|
| 4,515,595 | 5/1985 | Kievit et al. . |
| 4,517,714 | 5/1985 | Sneed et al. . |
| 4,531,999 | 7/1985 | Persson et al. . |
| 4,537,591 | 8/1985 | Coates . |
| 4,543,154 | 9/1985 | Reiter . |
| 4,552,795 | 11/1985 | Hansen . |
| 4,600,618 | 7/1986 | Raychok et al. . |
| 4,604,315 | 8/1986 | McCall et al. . |
| 4,606,694 | 8/1986 | Meisel, Jr. et al. . |
| 4,640,859 | 2/1987 | Hansen et al. . |
| 4,654,246 | 3/1987 | Provost et al. . |
| 4,657,802 | 4/1987 | Morman . |
| 4,714,736 | 12/1987 | Juhl et al. . |
| 4,725,473 | 2/1988 | Van Gompel et al. . |
| 4,732,631 | 3/1988 | Shimizu . |
| 4.806,300 | 2/1989 | Walton et al. . |
| 4,834,742 | 5/1989 | Wilson et al. ............... 604/391 |
| 4,846,815 | 7/1989 | Scripps . |
| 4,854,984 | 8/1989 | Ball et al. . |
| 4,859,169 | 8/1989 | Walton et al. . |
| 4,894,060 | 1/1990 | Nestegard . |
| 4,919,738 | 4/1990 | Ball et al. . |
| 4,920,617 | 5/1990 | Higashinaka . |
| 4,973,326 | 11/1990 | Wood et al. ............... 604/391 |
| 5,032,122 | 7/1991 | Noel et al. . |
| 5,100,399 | 3/1992 | Janson et al. ............... 604/391 |

LOOP FASTENING MATERIAL FOR FASTENING DEVICE AND METHOD OF MAKING SAME

This application is a continuation-in-part of application Ser. No. 07/382,516, filed Jul. 19, 1989, and now abandoned that is entitled "Improved Method For Manufacturing A Laminate Having At Least One Pleated Lamina", which is a continuation-in-part of application Ser. No. 64,896, filed on Jun. 19, 1987, now U.S. Pat. No. 4,854,984.

FIELD OF THE INVENTION

The present invention relates to a loop fastening material for fastening devices and a method for producing such a loop fastening material and, more particularly, to a loop fastening material for use with disposable absorbent articles.

BACKGROUND OF THE INVENTION

Laminates having at least one pleated lamina are known in the prior art. For example, U.S. Pat. No. 4,377,431, issued Mar. 22, 1983, to Chodosh teaches a fabric having three substantially coextensive laminae, one lamina of which is pleated. The prior art also teaches the use of rolls 22 and 24 having circumferential grooves and lands to impart lateral stretch to a lamina, as, for example, shown by U.S. Pat. No. 4,517,714, issued May 21, 1985, to Sneed et al.

However, the prior art does not show a method to join at least two laminae in face to face relation, at least one lamina being pleated, to form a loop fastening material.

Fastening devices such as hook and loop-type fasteners are known and have gained wide acceptance. Such materials are generally known by the tradename 'Velcro' and are generally described in U.S. Pat. Nos. 2,717,437; 3,009,235; 3,266,113; 3,550,837; and 4,169,303. The hook and loop-type fastener comprises two mating fastening materials wherein a hook fastening material engages a loop fastening material. Engagement of the complementary mating hook and loop fastening materials will occur by placing the surface defined by the hook in face to face relationship with the surface defined by the loop. The fastener resists separation by shear stress and certain peel forces applied to the fastener during use but are readily separable by peel forces applied substantially normal to the plane of their engagement.

Such fastening devices have been found especially useful and favorable on disposable articles such as disposable garments, disposable diapers, disposable packages, cartons and the like. While such fastening devices provide a secure closing means, their use has, however, been limited on disposable articles due to the fact that such fastening devices are relatively costly. The major reason that such fastening devices are too costly is that they have high manufacturing costs. Thus, there is a need for a low-cost fastening device for such disposable articles.

While many attempts have been made to provide a low-cost fastening device, most of the efforts have been directed toward developing a low-cost hook fastening material. The loop fastening material remains a costly element for a fastening device for disposable articles. Loop fastening materials typically have a number of woven loops extending outwardly from a backing. The loops may be provided by weaving a base fabric containing supplementary warp threads or by knitting. However, these processes produce generally costly loop fastening materials due to the fact that these processes are relatively slow.

Thus, it is an object of the present invention to provide an improved fastening device for disposable articles.

It is another object of the present invention to provide an improved loop fastening material.

It is a still further object of the present invention to provide a low-cost and improved method for producing a loop fastening material.

These and other objects of the present invention will be more readily apparent when considered in reference to the following description and when taken in connection with the accompanying drawings.

SUMMARY OF THE INVENTION

The present invention provides a laminated loop fastening material for a refastenable mechanical fastening system, the loop fastening material being capable of engaging a complementary hook fastening material.

The loop fastening material is formed by a method comprising the steps of:

providing a first lamina and a second lamina, said first lamina having pleats and being fibrous;

providing a first roll and a second roll having mutually parallel axes and defining a nip therebetween, said first roll having a plurality of circumferential grooves and lands intermediate said grooves;

passing said first lamina and said second lamina through said nip in face to face relation, whereby said first lamina faces said first roll;

transversely registering the pleats of said first lamina with said grooves of said first roll;

pressing said first roll and said second roll together about the plane generally perpendicular to and connecting the axes of said first roll and said second roll so that said first lamina and said second lamina contact each other at a position corresponding to said lands; and bonding said laminae together at said positions of contact.

The present invention also relates to a fastening device having a hook fastening material and a loop fastening material. The loop fastening material comprises the improved loop fastening material of the present invention. The hook fastening material comprises any of the well known hook fastening materials as are known in the art and which have a base and a number of engaging elements extending from the base. The loop fastening material and the complementary hook fastening material provide a secure closing means that will resist shear stress and peel forces encountered during use.

The present invention also relates to disposable articles and more particularly to a disposable diaper having such an improved fastening device.

BRIEF DESCRIPTION OF THE DRAWINGS

While the Specification concludes with claims particularly pointing and distinctly claiming the present invention, it is believed the same will be better understood by the following description taken in conjunction with the accompanying drawings in which like parts are designated by the same reference numeral, related or analogous parts are designated with a prime symbol and:

DETAILED DESCRIPTION OF THE INVENTION

Figure 1:
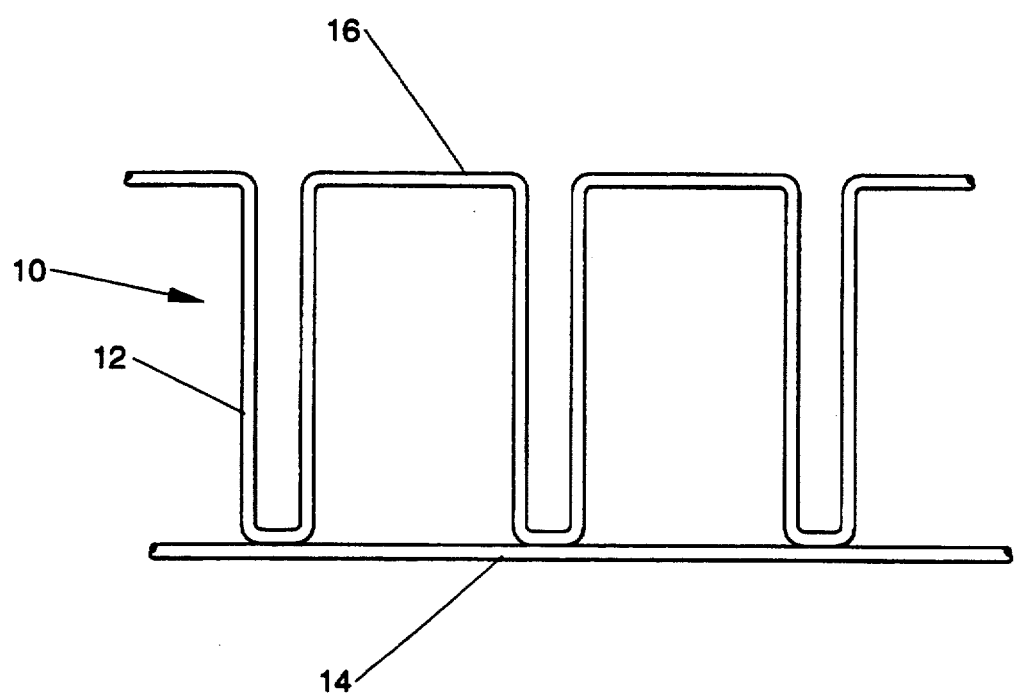
FIG. 1 is a vertical sectional view of a laminate produced according to the present invention and having one pleated lamina and one unpleated lamina.
Figure 2:
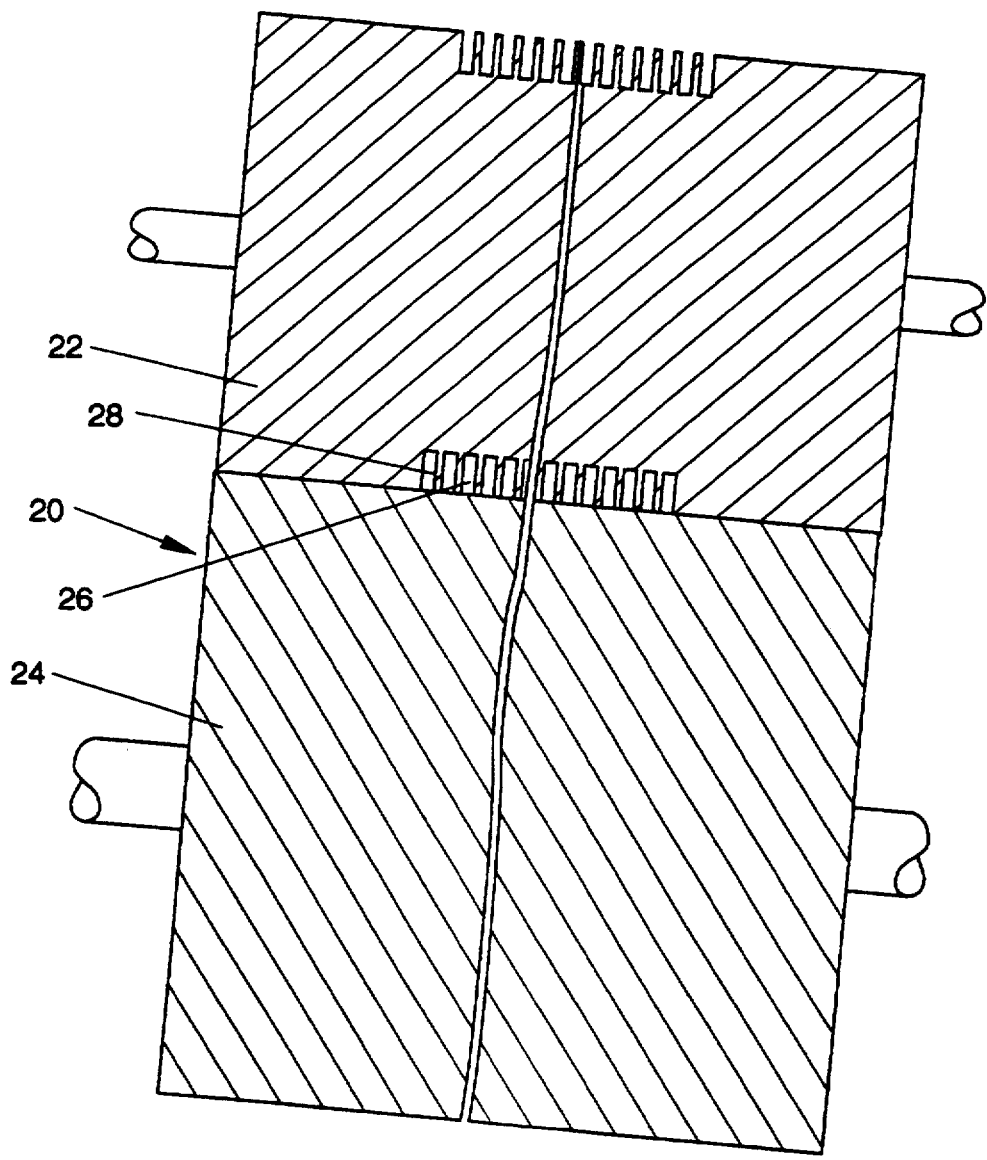
FIG. 2 is a vertical sectional view of an apparatus used to produce the laminate of FIG. 1, as viewed in the machine direction.

The present invention is directed to joining two laminae in face to face relation to produce a loop fastening material, unitary laminate 10, as illustrated in FIG. 1. The laminate 10 may also be referred to, herein, as the loop fastening material, the loop fastening laminate, the female fastener, the loop fastener or the fibrous fastening material. The first lamina 12 of the laminate 10 is the fibrous lamina and is pleated with pleats 16 oriented in the machine direction. The first lamina 12 may also be referred to, herein, as the fibrous lamina or the pleated lamina. The second lamina 14 is the backing lamina and is unpleated. The second lamina 14 may also be referred to, herein, as the backing lamina, the unpleated lamina, or the elastomeric lamina. The laminate 10 may be produced with the apparatus 20 illustrated by FIG. 2. The apparatus 20 comprises two rolls 22 and 24 and the nip defined therebetween.

Preferably, the rolls 22 and 24 have generally straight axes, although rolls 22 and 24 having curved axes (not shown) may be used with the present invention as well. The rolls 22 and 24 are disposed and rigidly held by a frame (not shown) as is commonly known in the art, so that the axes of the rolls 22 and 24 are mutually parallel. The frame may support both ends of the rolls 22 and 24, or the rolls 22 and 24 may be cantilevered from one end.

The first roll 22 is circumferentially grooved and the second roll 24 has a generally smooth, uninterrupted circumference. As used herein, the term "groove" refers to a channel in the roll 22, which channel extends substantially around the circumference of the roll 22. The bottom of the groove 26 is that face of the groove 26 which is of the least diameter. The sides of the groove 26 are those faces radially oriented and which extend from the bottom of the groove 26 to the outer circumference of the roll 22. The groove 26 may be of any suitable cross section, although a rectangular cross section, as shown, is generally preferred.

Figure 3:
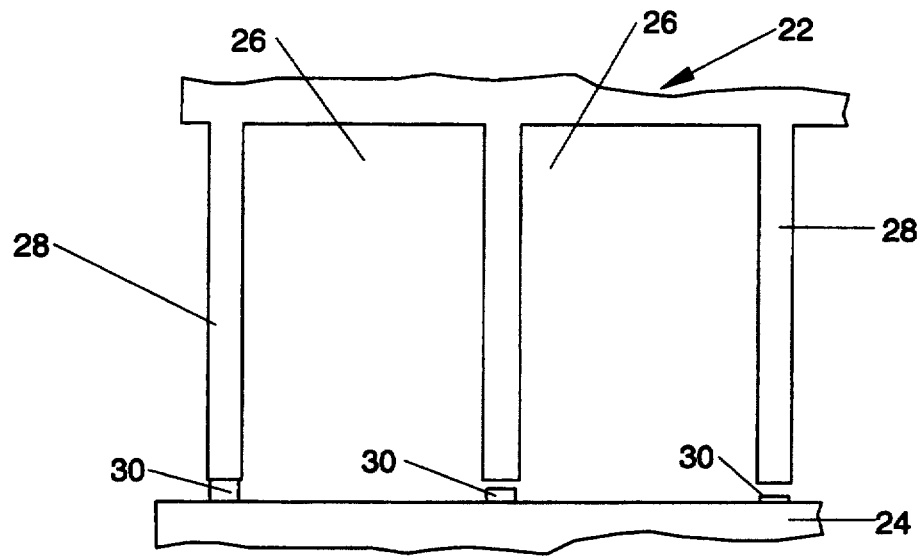
FIG. 3 is an enlarged view of a portion of the apparatus of FIG. 2, showing the grooves and lands.

As illustrated in FIG. 3, intermediate the grooves are lands 28. As used herein, the phrase "land" refers to any portion of the roll 22 intermediate two grooves 26 and which has a diameter greater than that than of the bottom of either adjacent groove 26. Each land 28 may be thought of as an annular cantilevered beam having a fixed end at the bottom of the grooves 26 and a free end at the outer circumference of the roll 22. It is not necessary that the land 28 be of constant diameter throughout the entire circumference. It is only necessary that the space between the grooves 26 be interrupted in diameter and that the grooves 26 are not contiguous. As used herein the "depth" of the groove 26 is the difference between the radius at the bottom of the groove 26 and the greatest radius of the outermost portion of the adjacent land 28. As used herein the term "pitch" refers to the distance, taken parallel to the axis of the roll 22, between the circumferential centerlines of adjacent grooves 26, or the distance between centerlines of adjacent pleats 16 of the pleated lamina 12.

Disposed on the distal end of the land 28 of the grooved roll 22 or on the periphery of the smooth roll 24 and registered with the lands 28 of the grooved roll 22 may be one or more generally radially oriented upstanding protrusions 30. The upstanding protrusions 30 may be generally cylindrically or rectangularly shaped, and provide discrete bonding points for the laminae 12 and 14 passing through the nip. The protrusions 30 have a height of about 0.5 millimeters (0.020 inches) and a diameter of about 0.5 millimeters to about 1.4 millimeters (0.20 inches). The rolls 22 and 24 are pressed together to effect joining the laminae 12 and 14. The protrusions 30 provide sites of increased compressive pressure, so that a more stable bond is obtained. Preferably, the protrusions 30 are not circumferentially registered, so that the bonding sights are transversely staggered on the resulting laminate 10.

The diameters of the rolls 22 and 24 are controlled by the compressive force used to urge the rolls 22 and 24 together and the length of the rolls 22 and 24. As either parameter increases, the minimum diameter of the grooved roll 22 (measured at the bottom of the grooves 26) must increase accordingly. The diameter of the roll 22 at the outer periphery of the lands 28 is then selected in accordance with the desired pleat height. The diameter of the second roll 24 is preferably different from, but no less than, the minimum diameter of the grooved roll 22—so that adequate strength is maintained, but the same points on the circumferences of the rolls 22 and 24 do not contact on each revolution. Generally as the difference between the diameter of the roll 22 at the bottom of the grooves 26 and the diameter at the circumference of the lands 28 increases, the lands 28 should be made wider to provide adequate strength and to preclude axial movement of the distal ends of the lands 28.

The width and pitch of the grooves 26 of the grooved roll 22 should correspond generally to the width and pitch of the pleats 16 of the pleated lamina 12. For pleats having a pitch less than about 0.17 inches, the grooves 26 may be about 10 percent wider than the desired pleats 16 to allow for variations in tracking and volume of the pleated lamina 12. Further, the grooves 26 should have a depth sufficient to accommodate the size of the pleats 16, otherwise wrinkling of the pleated lamina 12 may occur.

Pleat sizes ranging in height from about 0.8 millimeters to about 6.4 centimeters (0.03 inches to 0.75 inches) and grooves 26 having a pitch ranging from about 2.5 millimeters to 13 millimeters (0.10 inches to 0.50 inches) work well with the method disclosed herein. Thus the grooves 26 may advantageously be made of any size within this range, or of other sizes and geometries as desired.

The second roll 24 is relatively smooth, being ungrooved, corresponding to the second lamina 14 of the laminate 10. Generally as the force compressing the first and second rolls 22 and 24 increases, or the length of the rolls 22 and 24 increases, a larger diameter second roll 24 is desired. Alternatively, the second 24 roll may be slightly bowed towards the first 22 roll so that constant surface interface is maintained between the rolls 22 and 24.

Each roll 22 and 24 is free to rotate about its respective axis. The rolls 22 and 24 rotate in the opposite sense—so the circumferences of the rolls 22 and 24 are traveling in substantially the same direction at the nip. Preferably, both rolls 22 and 24 are externally driven, particularly as higher processing velocities are utilized. Alternatively, the first roll 22 may be externally driven, and the second roll 24 rotated by the tangential frictional component of the laminae 12 and 14 passing through the nip. The laminae 12 and 14 may pass through nip at a velocity of about 120 to about 310 meters per minute (400 to 1,000 feet per minute). For speeds of about 120 meters per minute, or greater, a motor of about 7500 watts for each roll 22 and 24 is suitable. It is not, however, necessary that the surface velocity of the rolls 22 and 24 be matched.

The laminae 12 and 14 are held in face to face relation and pass through the nip in the machine direction. As used herein, the term "machine direction" refers to that direction generally perpendicular to both axes of the rolls 22 and 24 and the plane which connects the axes of the rolls 22 and 24. Furthermore, as used herein, the term "cross machine direction" refers to the direction generally parallel to the axes of the rolls 22 and 24 and perpendicular to the machine direction. The "nip plane" is that plane generally perpendicular to the plane which connects the axes of the rolls 22 and 24 and which intercepts the nip of the rolls 22 and 24.

The laminae 12 and 14 may be composed of any material suitable for the end-use application. Generally, as the thickness of the pleated lamina 12 increases, the pitch of the grooves 26 should increase to accommodate the greater amount of material present. The process described herein is successfully used with elastomeric, paper and polyolefinic laminae 12 and 14, such as polypropylene and polyethylene. The pleated lamina 12 may have a thickness ranging from about 0.02 millimeters to about 0.5 millimeters (0.0008 inches to 0.02 inches). The pleated lamina 12 may be a nonwoven material. A preferred material for use as the pleated lamina 12 of the loop fastening material 10, is a polypropylene nonwoven material having a basis weight of about 5 grams/square yard (6.0 grams/square meter) to about 30 grams/square yard (35.9 grams/square meter) and having a denier in the range of 2 to 15. A particularly preferred material for use as the pleated lamina 12 of the loop fastening laminate 10, is a polypropylene nonwoven material having a basis weight of about 10 grams/square yard (12 grams/square meter) to about 18 grams/square yard (21.5 grams/square meter) and having a denier in the range of 3 to 10. The unpleated lamina 14 may be elastomeric. The unpleated lamina 14 may be a nonwoven material, but is preferably a film. A particularly preferred material for use as the unpleated lamina 14 of the loop fastening laminate 10 is a polypropylene film having a thickness of about 0.0015 inches (0.038 millimeters).

The first lamina 12 is pleated, using any means well known in the art for providing "pleats", i.e. portions displaced from the plane of the lamina 12, which pleats are oriented substantially parallel to the machine direction. Suitable pleating methods are disclosed in U.S. Pat. No. 4,252,591, issued Feb. 24, 1981 to Rosenburg, and Canadian Patent 758,794, issued May 16, 1967 to Ives et al., which patents are incorporated herein by reference for the purpose of showing suitable methods to provide machine direction oriented pleats. The second lamina 14 is used in a relatively smooth, unpleated condition.

The laminae 12 and 14 are preferably supplied from individual supply rolls 22 and 24 (not shown). Each supply roll is mounted with its respective axis generally parallel that of the rolls 22 and 24 and upstream of the nip. The laminae 12 and 14 are brought together in face to face relation either by using tracking rolls (not shown) or directly through the nip of the rolls 22 and 24. The laminae 12 and 14 may be pulled through the nip by takeup rolls 22 and 24 (not shown). The laminae 12 and 14 may pass through the nip at the same surface velocity or, if desired, at a different surface velocity, The pleated lamina 12 is transversely registered with the grooves 26 so that preferably the centerline of each pleat 16 is aligned with the centerline of each groove 26. This may be accomplished by transversely adjusting the position of the supply roll, or the position of the last roll which the pleated lamina 12 crosses, relative to the position of the grooved roll 22. Such adjustment may be accomplished by axial movement of either the supply roll or the grooved roll 22. It is important that the pleated lamina 12 travel through the nip in a direction parallel to the machine direction, otherwise wrinkling and bunching of the lamina 12 within the grooves 26 and at the nip may result. Therefore, the axis of the supply over for the pleated lamina 12 should be generally parallel to the nip.

It is important that the pleated lamina 12 not become wrinkled or transversely misregistered with the grooves 26 of the grooved roll 22. If this occurs, the pleats 16 may become laterally tensioned and a laminate 10 of uniform pitch and the desired aesthetics may not result. Typically, if the pleats 16 should become laterally tensioned (e.g. due to a geometry mismatch with the grooves 26 of the first roll 22 or not being registered with the grooves 26) a relatively large pleat 16 will result at the point the pleated lamina 12 was tensioned and a relatively small pleat 16 will result elsewhere, due to the relative loss and transfer of material necessary to form the larger pleat 16.

The position of the unpleated lamina 14 relative to the nip is not critical. It is only necessary that the transverse ends of the laminae 12 and 14 be coterminous, otherwise the resulting laminate 10 will have a single lamina at each edge. Although it is not critical, the unpleated lamina 14 should pass through the nip generally parallel to the machine direction, otherwise the unpleated lamina 14 may not be properly joined to the pleated lamina 12.

The confluent laminae 12 and 14 are joined at the nip or after passing through the nip. The laminae 12 and 14 may be joined by adhesive or autogenous bonding. If adhesive bonding is selected, the adhesive is applied to the face of either lamina 12 or 14 which is oriented towards the other lamina 12 or 14. Preferably the adhesive will be applied to the unpleated lamina 14. Alternatively, an adhesive lamina (not shown) may be interposed between the pleated 12 and unpleated lamina 14 so that a laminate 10 having three laminae is formed; with a central lamina of adhesive and two outboard laminae 12 and 14, one pleated, one unpleated, as described above. One suitable method for producing such a three laminae laminate 10 is disclosed in U.S. Pat. No. 4,377,431 issued Mar. 22, 1983, to Chodosh and incorporated herein by reference for the purpose of showing how to produce such a laminate 10. Pressure sensitive adhesive marketed by The Century Adhesives Company of Columbus, Ohio as a diaper chassis adhesive has been found to work well for adhesive joining of the laminae 12 and 14.

Alternatively, a three (or more) laminae laminate 10 having a nonadhesive central lamina may be formed. If a nonadhesive central lamina is selected, the three (or more) laminae may be joined by autogenous bonding.

If autogenous bonding is selected, it may be accomplished by heating the rolls 22 and 24 and pressing the rolls 22 and 24 together about the plane generally perpendicular to and connecting the axes of the rolls 22 and 24. Additionally, the laminae 12 and 14 may be drawn through the nip at a differential velocity of about 2% to about 40% of the velocity of the lamina 12 or 14 having the lower velocity at the plane of the nip. Autogenous bonding, as described in U.S. Pat. No. 4,854,984, issued to Ball et al. on Aug. 8, 1989, has been found suitable, which application is incorporated herein by reference for the purpose of showing a particularly preferred method of autogenous bonding.

The rolls 22 and 24 may be pressed together so that a pressure of about 42,200,000 to about 56,200,000 kilograms per square meter (60,000 to 80,000 pounds per square inch) is obtained and the laminae 12 and 14 are brought into contacting relationship at the positions of the lands 28. The pressure is measured by dividing the compressive force applied to the rolls 22 and 24 by the area of the protrusions 30 at the bonding footprint. The bonding footprint is obtained by inserting an unpleated stationary lamina 14 between the rolls 22 and 24 and compressing the rolls 22 and 24 with a known force until an impression on the lamina 14 is obtained from each protrusion in the vicinity of the nip. The area of each protrusion and the number of impressions are counted and summed to yield the effective bonding area. This area is divided into the applied force to yield the compressive pressure on the roll 22 or 24 having the protrusions 30.

A nonlimiting example of the process disclosed herein found suitable for producing a laminate 10 having two laminae 12 and 14, one pleated, one unpleated is as follows. A first lamina 12 having pleats of about 9.5 millimeters (0.38 inches) height, about 4.7 millimeters (0.19 inches) width, and a pitch of about 6.4 millimeters (0.25 inches) is provided. The second lamina 14 is unpleated and generally smooth. Both laminae 12 and 14 are made of a thermoplastic material, particularly polypropylene. The first lamina 12 is a polypropylene nonwoven material of about 2.2 denier and a basis weight of about 24 grams per square meter (20 grams per square yard). The second lamina 14 is a polypropylene film having a thickness of about 0.2 millimeters (0.008 inches).

Two rolls 22 and 24 are provided. The first roll 22 is grooved, with grooves 26 of about 9.5 millimeters (0.38 inches) in depth, about 4.7 millimeters (0.19 inches) in width and of about 6.4 millimeters (0.25 inches) in pitch. The maximum diameter of the roll 22 is about 15.2 centimeters (6 inches) and the diameter at the bottom 26 of the grooves is about 14.0 centimeters (5.5 inches). The second roll 24 is not grooved and has a diameter of about 29 centimeters (11.4 inches). Both rolls 22 and 24 have straight and mutually parallel axes, and are about 33 centimeters (13 inches) long.

The second roll 24 has 36 equally spaced protrusions 30 corresponding to the axial position of each land. Each protrusion 30 is about 3.8 millimeters (0.015 inches) in radial dimension and has a parallelogram shaped surface of about 1.9 square millimeters (0.003 square inches). The rolls 22 and 24 are pressed together with a force of about 2500 kilograms (5600 pounds), so that a pressure of about 49,200,000 kilograms per square meter (70,000 pounds per square inch) is obtained on the raised protrusions 30 of the circumferentially grooved roll 22.

The laminae 12 and 14 are drawn through the nip defined by the rolls 22 and 24 at a uniform and constant velocity of about 180 meters per minute (600 feet per minute). Both rolls 22 and 24 are heated to a surface temperature of about 82° C. to provide for autogenous bonding of the laminae 12 and 14. The resulting laminate 10 has pleats 16 of generally uniform pitch, height, and width.

Figure 4:
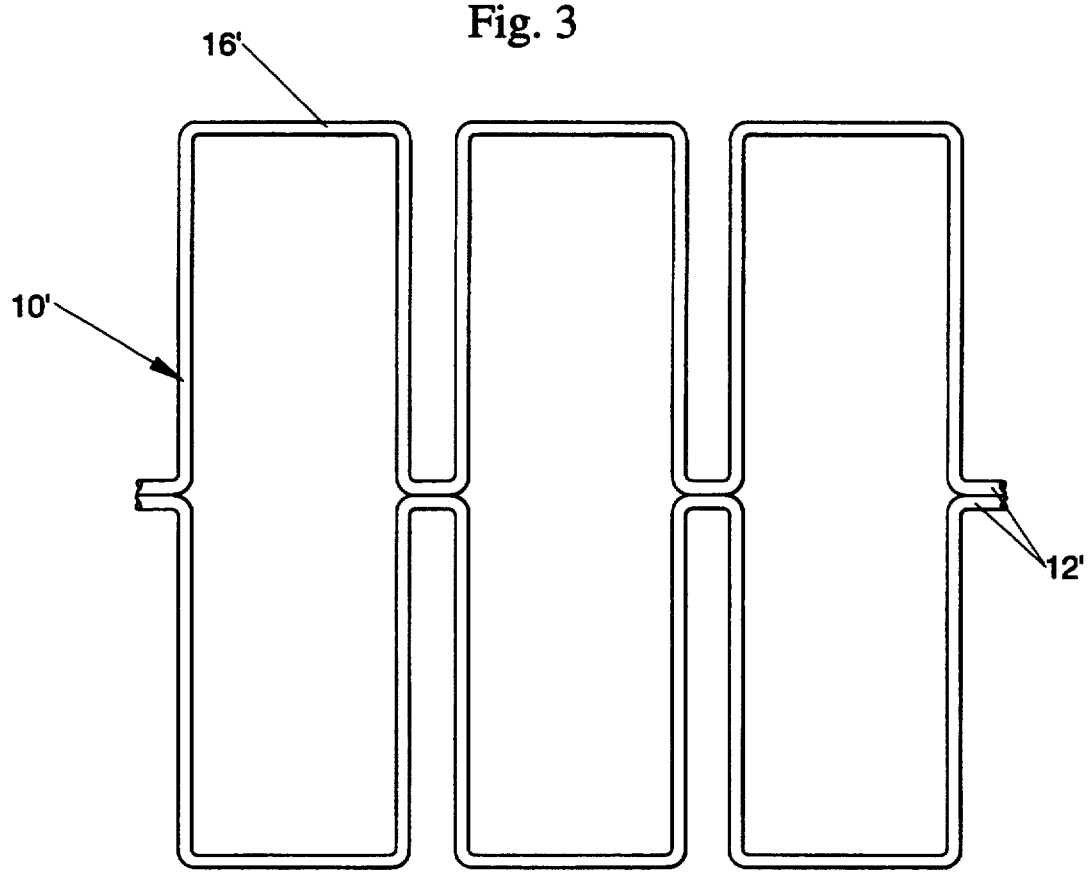
FIG. 4 is a vertical sectional view of a laminate produce according to the present invention and having two pleated laminae.
Figure 5:
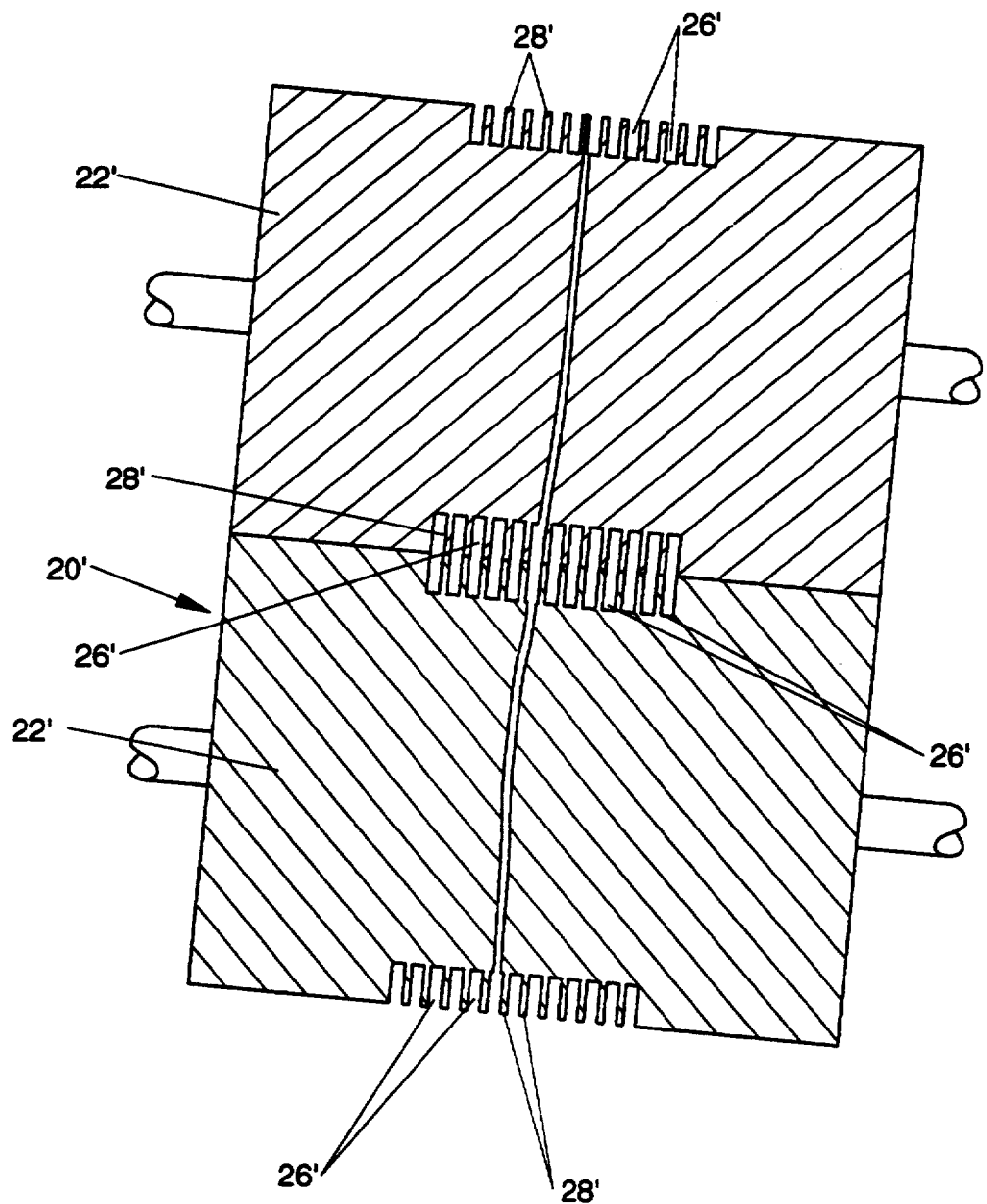
FIG. 5 is a vertical sectional view of an apparatus used to produce the laminate of FIG. 4, as viewed in the machine direction.

Variations in the disclosed method of producing a pleated laminate 10 are feasible. For example, as shown in FIG. 4, a laminate 10 having two pleated laminae 12', each with oppositely facing machine direction oriented pleats 16' can be produced by the method described herein. Referring to FIG. 5, to produce such a laminate 10', it is only necessary two grooved rolls 22' and the nip defined therebetween, be provided, and that at least two, and preferably more, of the lands 28' of the grooved rolls 22' be transversely registered.

Two laminae 12' having longitudinal pleats made of either the same or different materials, and formed as described above, are provided and confluently passed through the nip in face to face relation with the pleated surfaces of the laminae 12' facing outwardly and oppositely from each other. The pleats 16' of the laminae 12' are matched in geometry to the circumferential grooves 26' of the rolls 22' and transversely registered as described above. The laminae 12' are then joined, either adhesively or autogenously as described above.

Figure 6:
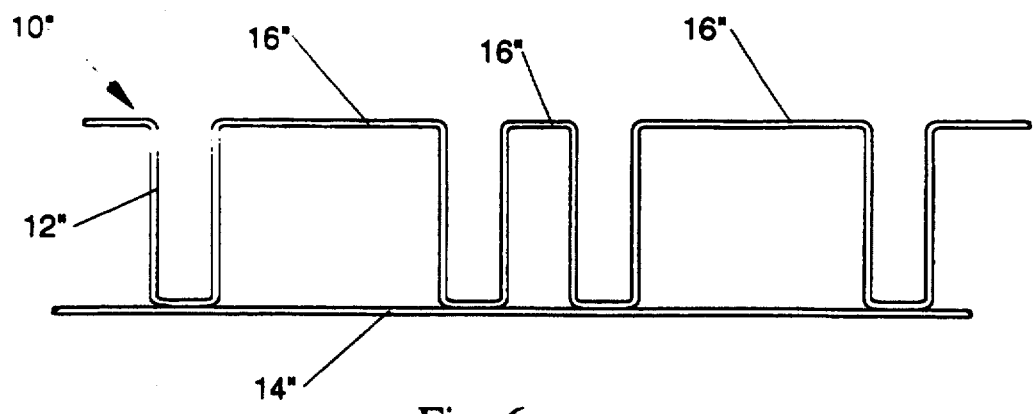
FIG. 6 is a vertical sectional view of a laminate produce according to the present invention having one pleated lamina of non-uniform pitch.
Figure 7:
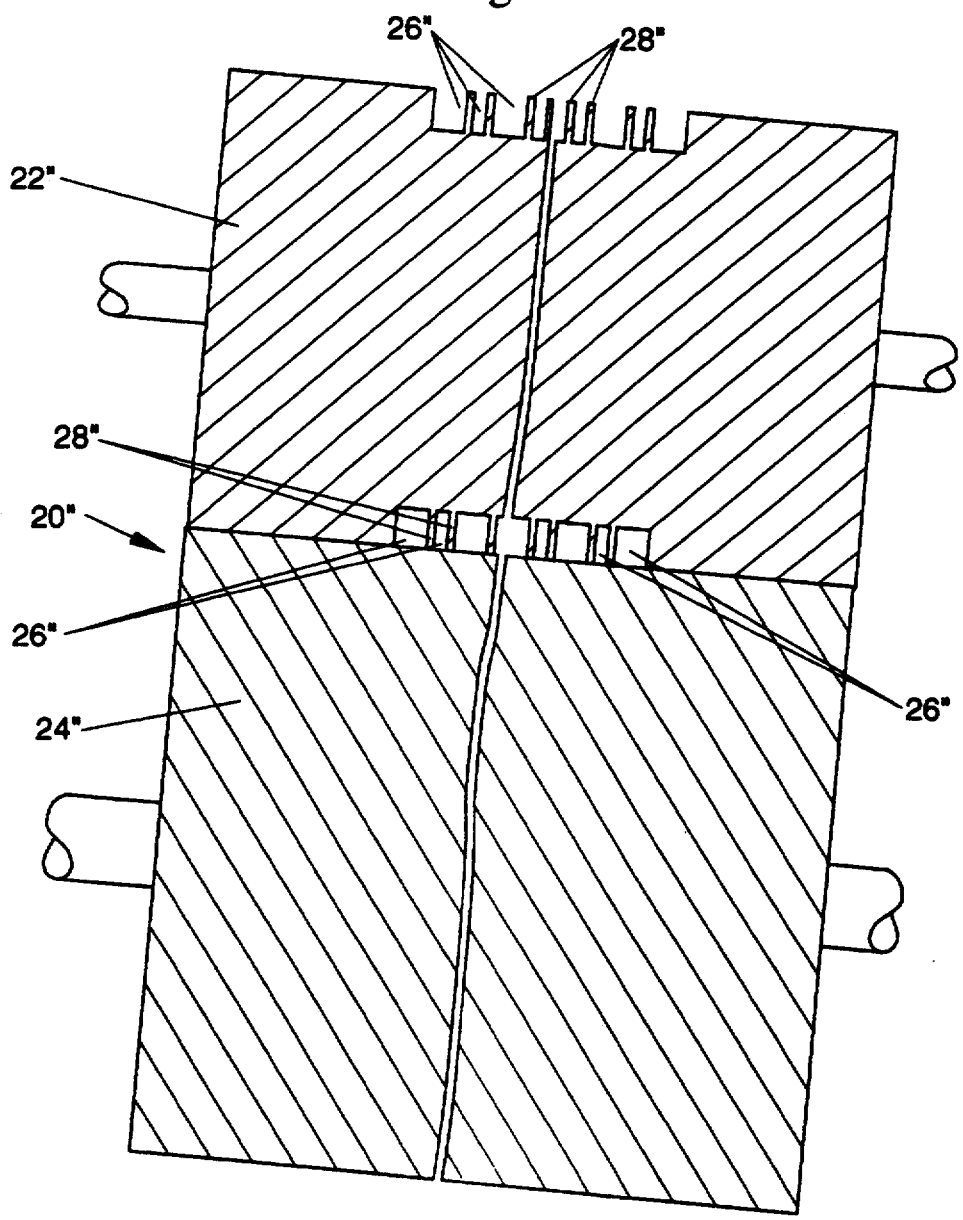
FIG. 7 is a vertical sectional view of an apparatus used to produce the laminate of FIG. 6, as viewed in the machine direction.

In another variation of the method of making the first above-described laminate 10, a laminate 10" having a pleated lamina 12" of nonuniform pitch, and a unpleated lamina 14" results, as illustrated in FIG. 6. Referring to FIG. 7, to produce such a laminate 10", a circumferentially grooved roll 22" having a nonuniform pitch, i.e. the spacing between adjacent grooves 26" varies along the axial length of the roll 22", is provided. A roll 24" which is not grooved is also provided. A first lamina 14" is provided, having pleats 16" of nonuniform pitch, corresponding to the width and pitch of the grooves 26" of the first roll 22". The first lamina 12" and a second unpleated lamina 14" are confluently passed through the nip in face to face relation as described above. This process yields a laminate 10" having one lamina 12" with spaced pleats 16" of a nonuniform and variable pitch and one unpleated lamina 14". Thus, the grooves 26" of the grooved roll 22" may either be spaced on a uniform pitch or on a nonuniform pitch.

It will be apparent to one skilled in the art, that the two variations described above may be combined to produce a laminate 10' having two laminae 12' with outwardly facing pleats 16' of a different but uniform pitch or having one or two nonuniform pitches. This execution may be combined with the three laminae laminate 10, discussed above, so that a laminate 10' having two pleated outboard laminae 12' and a central unpleated lamina results.

Another feasible variation is to utilize elastically extensible laminae 12 and particularly 14, extensible perpendicular to the pleats 16, so that the resulting laminate 10 has elastic properties and may be stretched. A preferred elastically extensible embodiment has an unpleated elastomeric lamina 14 joined to a pleated lamina 12. The unpleated lamina 14 may be stretched either before or after being joined to the pleated lamina 12. Another preferred elastically extensible embodiment has two outboard pleated laminae 12' and a central elastomeric unpleated lamina.

If the unpleated lamina 14 is stretched in the machine direction prior to bonding, or if the pleated and unpleated laminae 12 and 14 or both pleated laminae 12' are extensible in the direction generally parallel to the pleats 16, a laminate 10 or 10' having bielastic properties may be produced and stretched parallel or perpendicular to the pleats 16. It will be further apparent, that other variations in the method disclosed herein and laminate 10 produced hereby may be made without departure from the spirit and scope of this invention.

Figure 8:
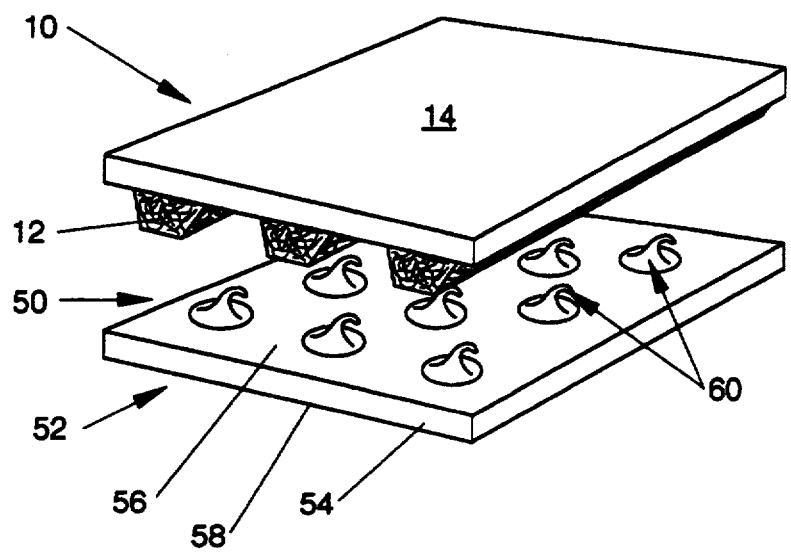
FIG. 8 is a perspective view of a fastening device according to the present invention.

The loop fastening laminate 10 is intended to be one component of a refastenable mechanical fastening device 50 shown in FIG. 8. The fastening device 50 preferably comprises the loop fastening material 10 of the present invention and a complementary hook fastening material 52 engageable with the fibrous lamina 12 of the loop fastening material 10. As used herein, the term "hook fastening material" is used to designate the portion of the fastening device 50 having engaging elements. Thus, the hook fastening material may also be referred to as the male fastener. It should also be understood that the use of the term "hook" should be nonlimiting. The engaging elements may comprise any shape such as hooks, "T's", mushrooms, or any other shape as are well known in the art so long as they are adapted to engage a complementary loop fastening material. An exemplary hook fastening material is described in U.S. Pat. No. 4,846,815 entitled "Disposable Diaper Having An Improved Fastening Device" issued to Scripps on Jul. 11, 1989, and which patent is incorporated herein by reference.

An especially preferred hook fastening material comprises an array of prongs formed of thermoplastic material. Hot melt adhesive thermoplastics, in particular polyester and polyamide hot melt adhesives, are particularly well suited for forming the prongs of the hook fastening material. The prongs are preferably manufactured using a modified gravure printing or screen printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This preferred hook fastening material and methods and apparatus for making such a hook fastening material are more fully detailed in U.S. Pat. No. 5,058,247, issued Oct. 22, 1991 to D. A. Thomas and T. L. Blaney which patent is incorporated herein by reference.

As shown, the hook fastening material 52 preferably comprises a base 54 having a first surface 56 and a second surface 58 and a plurality of engaging elements 60 extending from the first surface 56 of the base 54.

Figure 9:
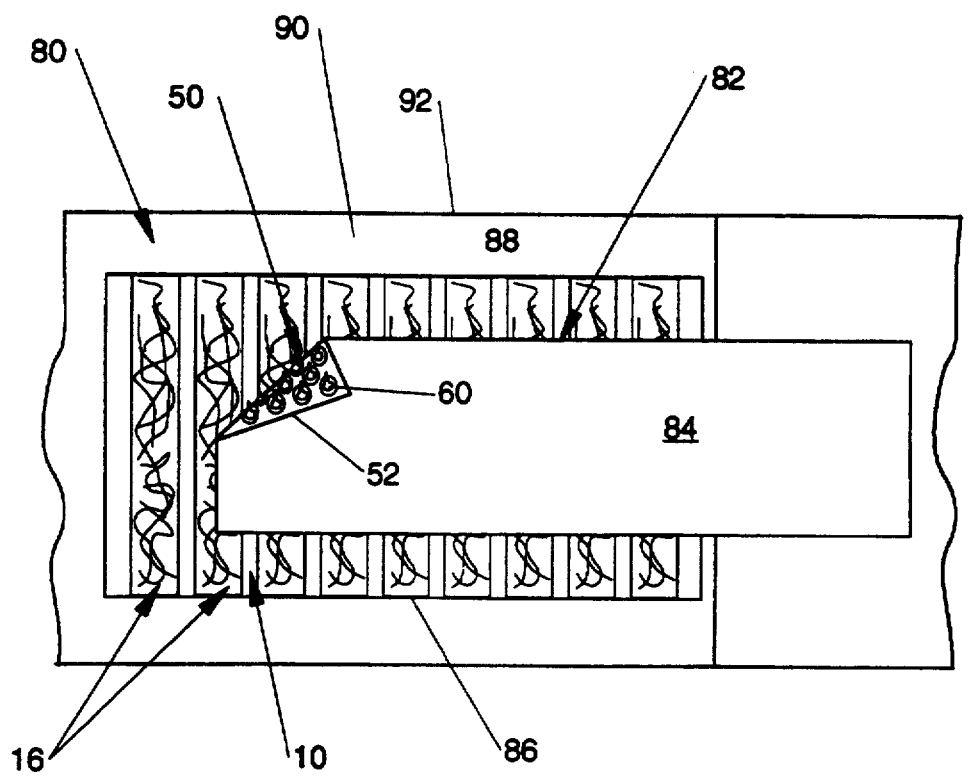
FIG. 9 is an enlarged perspective view of a tape fastening system of a disposable diaper incorporating the loop fastening material of the present invention.

In use, the hook and loop fastening materials are pressed face to face against each other so that the fibrous pleats 16 of the loop fastening material 10 "catch" on the engaging elements 60 of the hook fastening material 52. With the fibrous pleats 16 thus "hooked" or caught by the engaging elements 60 as is shown in FIG. 9, the connection between the elements resists shear stress and certain peel forces applied to the fastening device 50. The fastening device 50 is separated by peeling the hook fastening material 52 away from the loop fastening material 10 such that the fibrous pleats 16 are released, or broken. Thus, the hook fastening material 52 is completely detached from the loop fastening material 10.

The fastening device 50 of the present invention has been found to be especially useful for providing a fastening device for disposable articles. The loop fastening material can be made relatively inexpensively in comparison to the woven loops used in known fastening devices. In addition, since the fastening device on a disposable article is opened and closed far fewer times than on reusable articles, the loop fastening material is more suited for disposable articles since it need only be strong enough to provide a limited number of secure closures (10–20 times). It should be noted, however, that the loop fastening material can be made much stronger for use on durable articles or for any other contemplated use by, for example, increasing the diameter or denier of the filaments of the fibrous material of the first lamina 12. Thus, the fastening device 50 is especially useful on such disposable articles as packaging, disposable absorbent articles, disposable wraps or any other disposable material.

As shown in FIG. 9, the fastening device 50 is preferably positioned on a disposable absorbent article such as a disposable diaper 80. The disposable diaper 80 preferably comprises a liquid pervious topsheet, an absorbent core, a liquid impervious backsheet and elastic members. While the topsheet, the absorbent core, the backsheet and the elastic members may be assembled in a variety of well known configurations, a preferred disposable diaper configuration is described in U.S. Pat. No. 3,860,003 entitled "Contractible Side Portions For Disposable Diapers" which issued to K. B. Buell on Jan. 14, 1975 and which patent is incorporated herein by reference.

As shown in FIG. 9, the tape fastening system 82 of the diaper 80 preferably comprises the fastening device 50 of the present invention. Any of the well known configurations and constructions may be used as the tape fastening system. A preferred tape fastening system is a Y-tape as described in detail in U.S. Pat. No. 3,848,594 entitled "Tape Fastening System For Disposable Diaper" which issued to K. B. Buell on Nov. 19, 1974 and which patent is incorporated herein by reference. Alternatively preferred tape fastening systems are described in detail in European Patent Application 0 233 704 A2, The Procter and Gamble Company, published Aug. 26, 1987; U.S. Pat. No. 4,699,622 entitled "Disposable Diaper Having An Improved Side Closure" issued Oct. 16, 1987 to J. W. Toussant and M. H. Hasse; previously referenced U.S. Pat. No. 4,846,815 which issued on Jul. 11, 1989 to C. L. Scripps; and U.S. patent application Ser. No. 07/714,476, entitled "Absorbent Article with Fastening System Providing Dynamic Elasticized Waistband Fit", filed Jun. 13, 1991 in the name of Weil et al.; all of which are incorporated herein by reference.

The preferred tape fastening system illustrated in FIG. 9 has a tape tab 84 and a second member 86. Preferably, the tape tab 84 comprises the hook fastening material 52 having the engaging elements 60 extending from the tape tab 84. The second member 86 preferably is disposed on the outside surface 88 of the waist portion 90 of the diaper 80. In the preferred embodiment of the disposable diaper 80, the loop fastening material 10 of the present invention comprises the second member 86. As shown, the loop fastening material 10 preferably is oriented on the waist portion 90 of the diaper 80 with the pleats 16 extending essentially perpendicular to the end edge 92 of the diaper 80. (Perpendicular to the direction of shear forces applied to the fastening device during use.) Thus, in this configuration the fibrous pleats 16 provide the maximum peel and shear force resistance. The loop fastening material 10 may, however, be oriented on the waist portion 90 in any configuration such as with the pleats 16 extending parallel to the end edge 92 of the diaper 80 or at any angle to the end edge 92.

It is also possible to form the diaper 80 such that the backsheet of the diaper 80 forms the unpleated lamina 14 of the loop fastening laminate 10. This would result in the entire outside surface 88 of the diaper 80 being a loop fastening laminate 10 and would provide a soft, comfortable outer surface to the diaper 80. In another variation, the backsheet of the diaper 80 may be an elastomeric material which forms the unpleated lamina 14 of the loop fastening laminate 10. This would result in a stretchable diaper 80 having a soft, comfortable outer surface.

Particularly preferred elastomeric materials for use as the unpleated lamina 14 of the loop fastening laminate 10, are Kraton based elastomeric films which are available from the Exxon Chemical Company, 5200 Bay Way Drive, Baytown, Tex. 77520.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having end edges and a soft, comfortable outer layer, said absorbent article comprising a liquid pervious topsheet, a liquid impervious backsheet joined to said topsheet, an absorbent core positioned between said topsheet and said backsheet, and a fastening device positioned on the disposable absorbent article, said fastening device comprising:
   a hook fastening material comprising a base and a multiplicity of prongs joined to said base, each of said prongs being made of thermoplastic hot melt adhesive deposited onto said base; and
   a loop fastening material for engaging said prongs of said hook fastening material;
   said loop fastening material comprising:
      a fibrous lamina having pleats of nonuniform pitch, said fibrous lamina being bonded to said backsheet, said pleats extending in a direction perpendicular to said end edges of said disposable absorbent article, said backsheet being substantially entirely covered by said fibrous lamina to form a soft comfortable outer layer.

2. The disposable absorbent article of claim 1 wherein said backsheet comprises an elastomeric material.

3. The disposable absorbent article of claim 2, wherein said fibrous lamina is gathered perpendicular to said pleats.

* * * * *

UNITED STATES PATENT AND TRADEMARK OFFICE
CERTIFICATE OF CORRECTION

PATENT NO. : 5,380,313

DATED : January 10, 1995

INVENTOR(S) : David J. K. Goulait et al.

It is certified that error appears in the above-identified patent and that said Letters Patent is hereby corrected as shown below:

Column 7, line 16      delete ".".

Signed and Sealed this

Sixth Day of April, 1999

Attest:

Attesting Officer

Q. TODD DICKINSON

Acting Commissioner of Patents and Trademarks